(12) United States Patent
Lafon et al.

(10) Patent No.: US 6,379,320 B1
(45) Date of Patent: Apr. 30, 2002

(54) ULTRASOUND APPLICATOR FOR HEATING AN ULTRASOUND ABSORBENT MEDIUM

(75) Inventors: Cyril Lafon, Objat; Jean-Yves Chapelon, Villeurbanne; Dominique Cathignol, Genas; Frederic Prat, Villebon sur Yvette, all of (FR)

(73) Assignee: Institut National de la Santa et de la Recherche Medicale I.N.S.E.R.M., Paris (FR)

( * ) Notice: Subject to any disclaimer, the term of this patent is extended or adjusted under 35 U.S.C. 154(b) by 0 days.

(21) Appl. No.: 09/424,878

(22) PCT Filed: Jun. 11, 1998

(86) PCT No.: PCT/FR98/01212

§ 371 Date: Mar. 2, 2000

§ 102(e) Date: Mar. 2, 2000

(87) PCT Pub. No.: WO98/56462

PCT Pub. Date: Dec. 17, 1998

(30) Foreign Application Priority Data

Jun. 11, 1997 (FR) .............................. 97 07529

(51) Int. Cl.$^7$ ................................. A61H 1/00
(52) U.S. Cl. ................. 601/3; 601/2; 600/439; 600/462

(58) Field of Search ................................. 600/439, 462; 601/213

(56) References Cited

U.S. PATENT DOCUMENTS 5,529,572 A * 6/1996 Spector

* cited by examiner

Primary Examiner—Marvin M. Lateef
Assistant Examiner—Runa Shah Qaderi
(74) Attorney, Agent, or Firm—Dennison, Scheiner & Schultz

(57) ABSTRACT

An ultrasound applicator for heating, via an internal path, an ultrasound absorbent medium, includes an application head having a longitudinal axis and including at least one ultrasonic transducer having a planar emission face and an opposite face, a leakproof membrane which overlays and is spaced from the emission face, and which is transparent to ultrasound, and means for preventing propagation of ultrasound from the opposite face; means for remotely connecting the transducer to an electricity generator; and means for providing ultrasound coupling with the membrane. The planar emission face emits ultrasound waves through the membrane and in a direction that is substantially perpendicular to the emission face, such that the waves emitted are substantially planar and do not diverge in the vicinity of the transducer and the application head.

26 Claims, 2 Drawing Sheets

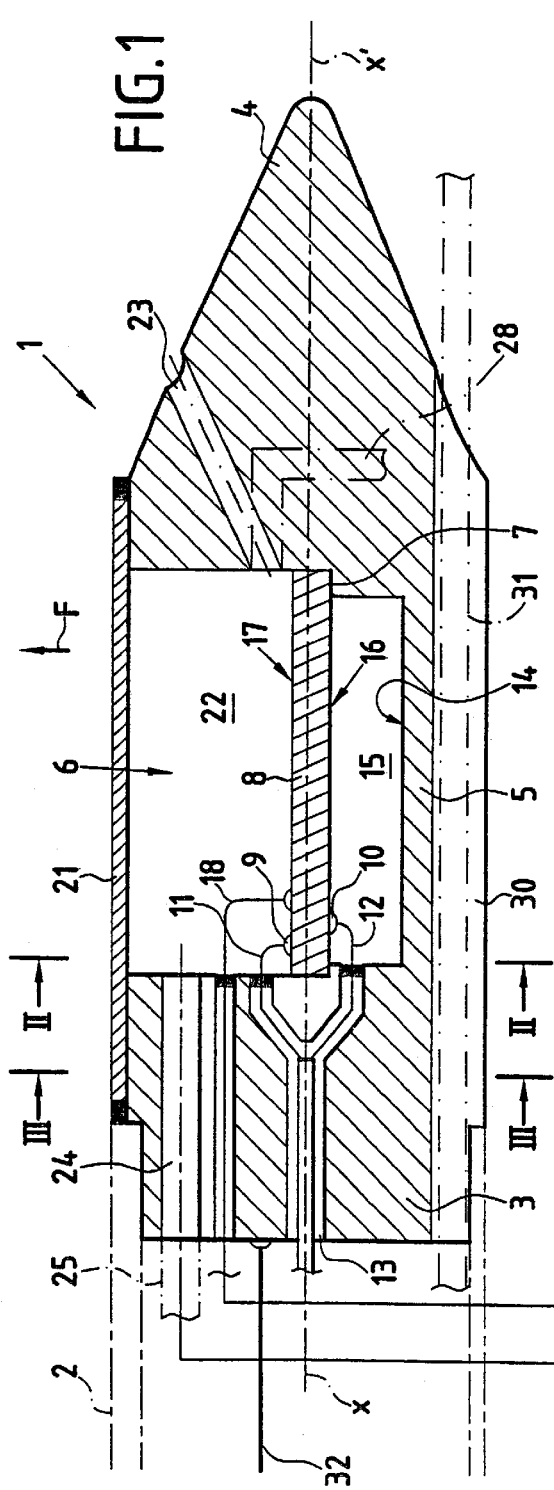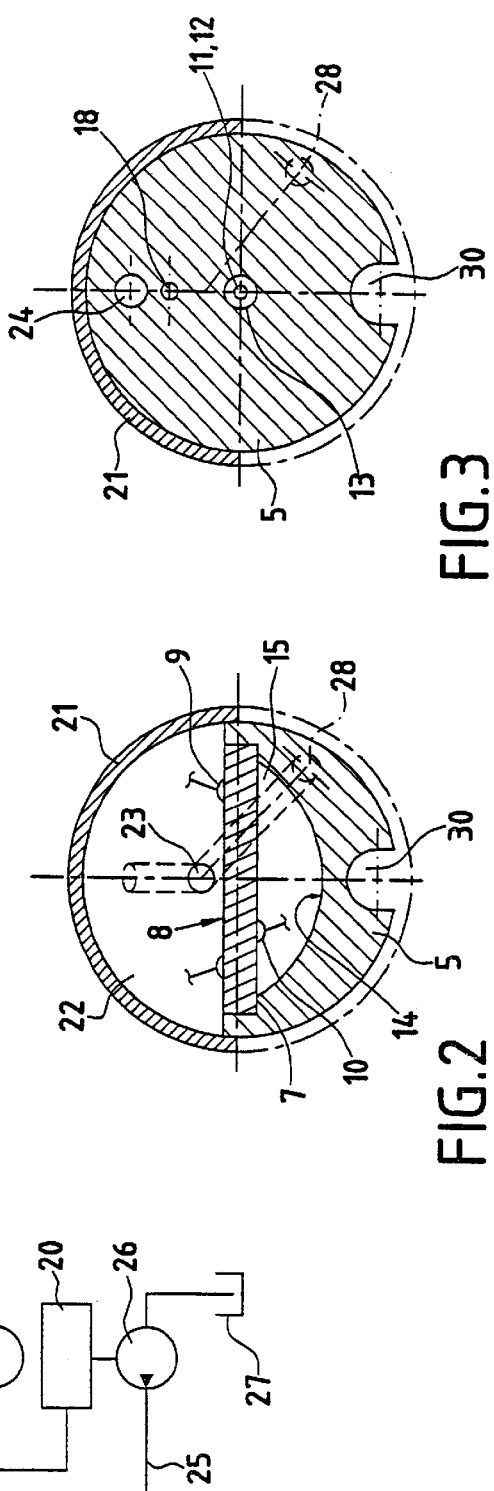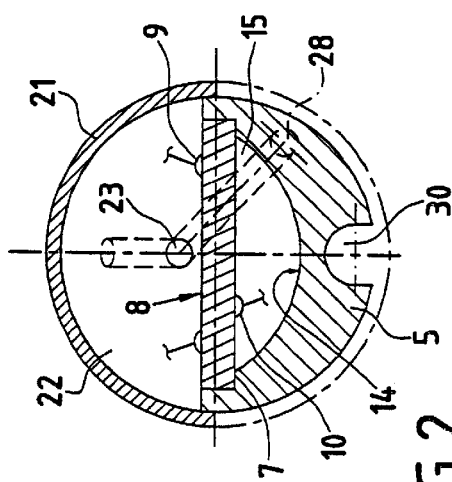

ULTRASOUND APPLICATOR FOR HEATING AN ULTRASOUND ABSORBENT MEDIUM

FIELD OF THE INVENTION

The present invention relates to devices used for localized hyperthermia treatment of tumors, generally malignant tumors.

In the above technical field, it is known to treat tumors by applying a local rise in temperature. Numerous publications mention the method which consists in raising the temperature of the zone concerned to around 45° C. so as to make the tissue sensitive to more traditional methods of treatment such as radiotherapy and chemotherapy.

Proposals have been made for some time now to treat tumors by heating the tissues to higher temperatures, around 80° C., in order to achieve necrosis by coagulation. The objective of this development is thus no longer to prepare tissues so that they have increased sensitivity to traditional methods of treatment, but is a direct attempt at destroying tissue by localized and controlled necrosis.

To carry out such a novel method of treatment with success, proposals have been made for applicators that have a head designed to deliver heat to the tissue concerned by implementing heat-production means that rely on various physical principles. In this respect, mention can be made of microwaves, ultrasound, heating resistance elements, lasers, etc.

DESCRIPTION OF RELATED ART

To undertake such treatment, the prior art comprises two kinds of proposal.

Proposals have been made for external hyperthermia applicators which are placed on the surface to treat tumors that are subcutaneous or at shallow-skin depth, or indeed directly accessible from the skin.

For tumors that are not accessible externally, proposals have also been made for "intratissular" applicators which are designed to be brought into the zone that is to be treated by endoscopic or endochannel means.

The present invention relates specifically to devices of the second kind, and thus concerns intratissular applicators, and more particularly applicators that use ultrasound to heat the zone(s) to be treated by means of an internal approach.

Publications which refer to such equipments describe applicators that produce an envelope of heat that is cylindrical or spherical, given the shape of the active portion of the applicator.

Thus, U.S. Pat. No. 5,620,479 describes an intratissular applicator comprising an application head that is substantially cylindrical in shape. The application head has a plurality of cylindrical ultrasound transducers connected to an electrical generator by conductor lines. The outside or emitting face of each transducer is in register with the wall of the application head which is transparent to ultrasound, while the inside face opposite from the emission face is in register with a volume of air.

Such application heads are characterized by the fact that the cylindrical transducers produce ultrasound waves that diverge, such that the quantity of heat produced, and therefore the rise in temperature, falls off very quickly with increasing distance from the heat-producing source. The effectiveness of treatment in depth in a given direction is therefore relatively limited, unless higher powers are used with the associated drawback of causing tissue in the vicinity of and/or in contact with the head to vaporize because of the increase in the amount of energy supplied by the applicator.

This gives rise to a difficulty of control in depth which is made all the more uncertain because the tissue concerned can be vascularized to a greater or lesser extent which is variable and random.

Another drawback associated with previously known applicators lies in the fact that cylindrical or spherical heads do not enable a privileged direction to be selected for treatment, and consequently do not give rise to coagulation necroses that are very well defined in a known field, i.e. that preserve the surrounding tissue which is not to be subjected to necrosis.

Another drawback of known applicators lies in the fact that the heat dispersion produced by application heads because of their omnidirectional diffusion needs to be compensated by proceeding with applications of long duration, giving rise to treatments that are relatively difficult, expensive to carry out, and highly dependent on the perfusion of the surrounding tissues.

To provide a solution to the problem of the dispersion of the emitted sound energy associated with the ultrasound waves generated by a cylindrical transducer diverging, the prior art has proposed implementing intratissular applicators having one or more transducers that generate ultrasound waves focused on one or more targets.

Thus, U.S. Pat. No. 5,402,792 describes an intratissular applicator having a head that is substantially cylindrical in shape defining a cavity in which there is placed a transducer whose emitting face is constituted by a concave acoustic lens having two acoustic focuses. The emitting face of the transducer is also covered at a distance by a leakproof membrane that is permeable to ultrasound, defining a cavity filled with degassed water to provide acoustic coupling between the emitting face and the membrane.

By using converging ultrasound waves, it is possible to concentrate the emitted acoustic-energy-in regions that are highly localized and of small extent. Nevertheless, given this small extent, it is essential to ensure that the applicator is positioned very accurately relative to the zone that is to be treated. Unfortunately, such accuracy is not always possible, depending on the region of the patient's body that is to be treated.

In addition, the ultrasound waves emitted by a focused transducer begin by converging on a focus, after which they diverge away from the focus, such that the acoustic radiation is not uniform and the quantity of heat produced falls off very quickly on going away from the focus and away from the transducer, as is the case for a cylindrical transducer.

SUMMARY OF THE INVENTION

The present invention seeks to remedy all of the above drawbacks by proposing a novel ultrasound applicator, preferably an intratissular applicator for localized application of hyperthermia, of a design which is selected to make it possible to deliver heat in a privileged direction while ensuring good penetration for the acoustic energy and also uniform distribution thereof, and while also making omnidirectional treatment possible where necessary.

Another object of the invention is to produce an ultrasound applicator which can be used easily via an endoscopic or endochannel path, being inserted directly into a natural passage or via the operative channel of an endoscope.

To achieve the above objects, the ultrasound applicator for internally heating an ultrasound-absorbing medium presents:

an application head having at least one ultrasound transducer with an "emission" face overlaid at a distance by a leakproof membrane that is transparent to ultrasound, and having another face, opposite to its emission face, that is associated with means that propagate ultrasound poorly or not at all;

means for remotely connecting the transducer to an electricity generator; and means for providing ultrasound coupling with the membrane.

According to the invention, the applicator is characterized in that the ultrasound transducer is plane and possesses a plane emission face for emitting substantially plane ultrasound waves in a direction substantially perpendicular to the emission face.

Another object of the invention is to provide means for controlling and regulating the temperature of the application head so as to make a large temperature rise possible without running the risk of forming microbubbles of vaporization.

According to another characteristic of the invention, the applicator includes means for cooling the transducer.

The invention also provides a method of heating an ultrasound wave absorbent medium, the method being of the type consisting:

in placing an applicator having at least one ultrasound transducer (8) in or close to said medium; and in emitting ultrasound waves from said transducer (8) in order to heat said medium.

According to the invention, the method is characterized in that it consists in implementing a plane transducer having a plane emission face for emitting ultrasound waves that are substantially plane in a direction that is substantially perpendicular to the emission face, and in heating the region of the absorbent medium that is situated in register with said emission face.

According to another characteristic of the invention, the method also consists in rotating the plane transducer so as to heat a larger volume starting from the same general position of the applicator.

According to another characteristic of the invention, the applicator then has means for rotating the transducer on its own or together with the application head.

The heating method and the applicator of the invention can be implemented specifically for localized treatment via internal passageways of regions in the human body that absorb ultrasound.

The invention thus also provides a method of therapy for applying hyperthermia treatment to a region of the human or animal body that absorbs ultrasound, the method being of the type consisting:

in placing an applicator having at least one ultrasound transducer in or in the vicinity of the region to be treated; and in emitting ultrasound waves from the transducer to heat said region.

According to the invention, the method consists in implementing a plane transducer having a plane emission face for emitting substantially plane ultrasound waves in a direction that is substantially perpendicular to the emission face and in heating the region situated in register with the emission face.

Various other characteristics appear from the following description given with reference to the accompanying drawings which show embodiments of the invention as non-limiting examples.

BRIEF DESCRIPTION OF THE DRAWINGS

FIG. 1 is a section view in elevation of an applicator of the invention.

FIGS. 2 and 3 are cross-sections on lines II—II and III—III of FIG. 1.

DESCRIPTION OF THE PREFERRED EMBODIMENTS

Figure 4:
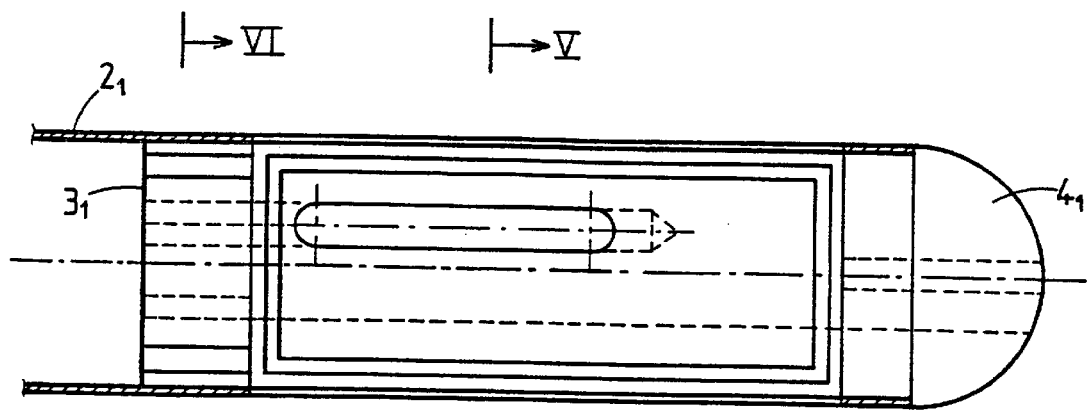
FIG. 4 is a plan view, partially in section, of another embodiment of the applicator.
Figure 6:
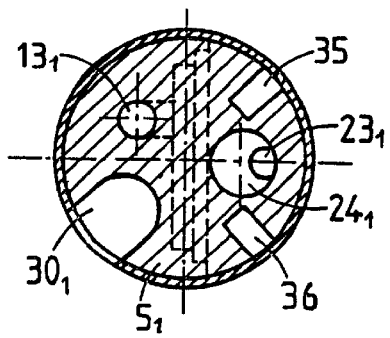
FIGS. 5 and 6 are cross-sections on lines V—V and VI—VI of FIG. 4.
Figure 5:
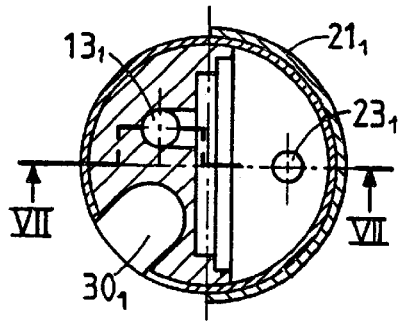

In FIGS. 1 to 3, the intratissular ultrasound applicator comprises an application head 1 which is preferably, but not exclusively, implemented using a non-ferromagnetic material so as to enable it to be used together with parallel treatment or monitoring installations that make use of the principle of nuclear magnetic resonance.

The head 1 is carried by a tubular element 2 which is constituted in this case by a rigid element fitted in any appropriate leakproof manner on the portion 3 of the head 1 which is considered as being a rear portion relative to a "penetration" front endpiece 4. It should be considered that the tubular element 2 could be constituted completely or in part by a flexible sheath, thereby facilitating controlled endoscopic or endochannel displacement. By way of example, such a sheath could advantageously be constituted by a succession of coaxial windings of wire in contiguous turns made from a wire of section that is circular or polygonal.

The head 1 has a body 5 forming the rear and front portions 3 and 4 between which there is a recess 6 which is open at least over a portion of the periphery of the body 5. In the application shown, the body 5 is preferably generally cylindrical in shape and the portion 4 is then advantageously in the form of a bullet, being frustoconical or conical, even though a spherical or hemispherical shape could be used.

The recess 6 is made so as to define, substantially in the middle of its depth in the example shown, a shoulder or seat 7 on which there can be mounted, fitted, or held in leakproof manner, a plane ultrasound transducer 8 that is generally rectangular in shape, having its length extending in the same direction as the longitudinal axis x—x' of the body 5, and more particularly parallel to said axis in the example shown.

The ultrasound transducer 8 is connected via surface connections 9 and 10 to two power supply wires 11 and 12 which are engaged through the rear portion 3 via a through hole 13 opening out into the recess 6. The power supply wires 11 and 12 are connected to a source of electricity (not shown) capable of applying frequencies of the order of 5 MHz to 10 MHz to the transducer. The transducer 8 can then be powered by an electrical signal at a single frequency or at multiple frequencies, depending on the nature of the desired ultrasound emission.

The way in which the transducer 8 is mounted in leakproof manner on the shoulder 7, and the position of the shoulder relative to the bottom 14 of the recess 6 are defined in such a manner that after the transducer has been put into place, it co-operates with the bottom 14 to define a chamber 15 which is filled with air in such a manner as to constitute means for preventing ultrasound from propagating from the rear large face 16 of the transducer 8.

This ensures that there exists a plane face from which emission is privileged, which face is constituted by the front large face 17, i.e. the face facing towards the opening of the recess 6 in the periphery of the body 5. Preferably, the plane emission face is of dimensions that are large enough to enable the transducer when in operation to emit ultrasound waves that are substantially plane and that do not diverge in the vicinity of the transducer and the applicator.

The ultrasound transducer 8 is associated with means for assessing its temperature rise. In the example shown, such means are constituted by a thermocouple 18 which passes through the rear portion 3 of the head 1 in leakproof manner so as to be connected to a visible display 19, e.g. a temperature gauge. The thermocouple 18 is preferably also coupled to a regulator 20 whose function appears below. The thermocouple 18 could be replaced by equivalent means, for example means for measuring variation in the electrical capacitance of the ultrasound transducer as a function of its temperature.

The recess 6 has its portion opening out to the periphery of the body 5 closed by means of a membrane 21 constituted by a sheet of material that has a low coefficient of attenuation for ultrasound. Advantageously, the membrane 21 is constituted by a sheet of low pressure polyethylene having a thickness of 12 $\mu$m and which is fitted to the body 5 by means of an appropriate adhesive, such as an adhesive of the cyanoacrylate type.

The membrane 21 can be constituted by a tubular segment that completely surrounds the body 5 or by a sectorial segment that covers the opening of the recess 6.

In co-operation with the face 17 of the transducer 8, the presence of the membrane 21 makes it possible to define a cavity 22 that is closed in leakproof manner inside the recess 6 and that is in communication firstly with a hole 23 formed in the portion 4 and opening out into the outside surface thereof, and secondly with a "feed" duct 24 passing through the rear portion 3. The duct 24 is connected to a tubular element 25 forming part of a circuit for circulating cooling fluid as delivered by a pump 26 from a supply 27. The cooling fluid can be of various kinds so long as it is selected to perform the function of providing ultrasound coupling between the transducer 8 and the membrane 21 while fully occupying the cavity 22. Preferably, such a fluid is constituted by degassed water.

The function of the pump 26, at least as concerns the flow rate it delivers, depends on the regulator 20 that monitors the temperature rise of the ultrasound transducer 8.

The fluid circulation circuit can comprise not only the go circuit 25, but also a return circuit 28 formed in the front portion 4 instead of the evacuation hole 23. Such a return circuit can then be connected directly to the source 27.

In general, the portion of the tubular element 2 that follows the rear portion 3 of the body of the head 1 is filled with material for occupying, sealing, and filling for the purpose of isolating, containing, holding, confining, and protecting the servo-control lines as constituted by the power supply wires 11 and 12, by the thermocouple 18, and by the circuit(s) 25.

Because of its shape, the above-described applicator can be inserted in the vicinity of or even inside the tumor that is to be treated via internal passageways, e.g. endoscopically or within a channel, so as to apply within said zone a rise in temperature that is created by ultrasound being absorbed in the absorbent medium or tissue situated in register with its emission face, once the transducer 8 has been connected to the source of electricity.

Because of the presence of the cushion of air occupying the chamber 15, the operation of the transducer 8 gives rise to ultrasound being emitted solely from its emission face 17 which produces a near field that is non-divergent, passing through the cavity 22 and the membrane 21 along a propagation direction that is normal to the plane of the emission face 17. The rise in temperature of the ultrasound transducer 8 due to the fact that its efficiency at converting electricity into sound is less than unity, is monitored by the means 18 which delivers information to the regulator 20 that enables the operating conditions of the pump 26 to be controlled so as to deliver cooling fluid at an appropriate rate into the inside of the cavity 22 which is kept full, with the cooling fluid either being evacuated via the hole 23 by natural perfusion into the tissue, or else being returned by the duct 28.

In this manner, it is possible to emit a powerful field without giving rise to a high localized rise in temperature which might otherwise cause the membrane to break by being overheated and/or cause microbubbles to be generated by boiling between the membrane 21 and the tissue which would have the effect of interrupting the propagation of ultrasound and consequently of destroying the ultrasound transducer.

By emitting a near field in a privileged direction that is substantially perpendicular to the emission face, as shown by arrow F, it is possible to undertake treatment that is selective, accurate, and localized on a tumor by means of an approach that is centralized or remote, and the tumor can also be treated in more complete manner by applying heat over a volume by subjecting the transducer 8 to rotation over an angular sector or through 360°. To this end, the applicator of the invention includes means for rotating the transducer. In the example shown, these means for rotation are constituted by a tubular element 2 which enables the application head 1 to be rotated about its axis x—x' and consequently enables the transducer 8 to be rotated. Preferably, the tubular element 2 has a high coefficient of resistance to twisting so as to enable the application head to be rotated appropriately.

The means for rotating the transducer can also be constituted by motor means or transmission means enabling rotation to be applied to the transducer on its own without simultaneously moving the application head. In preferred but non-exclusive manner, the transducer is rotated about an axis that is parallel to a long axis of its emission face. In addition, it should be observed that rotation of the transducer can take place continuously while emission is taking place in alternation or otherwise, for example rotation and emission can be sequential so as to cause the transducer to rotate stepwise, thereby successively heating zones that are contiguous.

It is also possible to proceed with displacement that is reciprocating or otherwise, rectilinear, and of varying amplitude along the axis x—x' of the head 1 so as to produce necrosis in a larger volume of tissue. Such displacement in translation of the head can also be combined with rotary movement of the transducer.

Thus, by using the means of the invention for monitoring and regulating temperature from the emission face 17 of the transducer 8, and by emitting a near field that is directional along arrow F, it becomes possible to perform localized hyperthermia treatment of tumors that may be of small volume or otherwise, at greater or lesser distance from the head 1, and by these means to perform treatments on tumors that would normally be considered, because of their specific locations, to be inaccessible to any possibility of localized application of hyperthermia.

By using a transducer that is 10 mm long by 3 mm wide and having a thickness of $\lambda/2$, where $\lambda$ is the wavelength, with the transducer being made of PZT 462 and suitable for operating at frequencies in the range 3 MHz to 20 MHz, is it possible to make an applicator having an outside diameter of about 3.6 mm making use of circuits 25 having a diameter of 0.8 mm suitable for maintaining a cooling fluid circulation in the cavity 22 at a rate of 7 milliliters per minute (ml/min).

Such means are suitable for applying a high temperature for a length of time that is short but nevertheless sufficient for achieving necrosis by coagulation.

The use of a transducer that has an emission face that is plane makes it possible to produce ultrasound waves that are substantially plane and that give rise to uniform and deep diffusion of sound energy in the absorbent medium.

In addition, given the plane nature of the waves emitted by a plane transducer, the transducer provides efficiency in terms of emitted acoustic power relative to power delivered to the transducer which is better than that provided by a cylindrical transducer of the prior art.

Thus, in the context of an in vivo test on the liver of a pig, an applicator of the invention implementing a plane transducer having dimensions of 10 mm×3 mm and powered by an electrical signal at a frequency of 10 MHz, so as to radiate power of 14 watts/cm$^2$ from its emission surface, has made it possible after emission for a duration of 20 seconds to obtain a lesion in register with the emitting face to a depth of 10 mm to 12 mm.

In contrast, in the context of an identical in vivo test, an applicator having outside dimensions identical to those of the above applicator but implementing a cylindrical transducer of the prior art having an outside diameter of 3 mm and a length of 10 mm, powered by an electrical signal at a frequency of 10 MHz so as to radiate power of 14 watts/cm$^2$ from its emission surface made it possible after emission having for a duration of 20 seconds to obtain a lesion in register with the cylindrical emission face of the transducer to a depth of only 2 mm to 3 mm.

It therefore appears, other things being equal, that implementing a plane transducer of the invention makes it possible, advantageously, to increase the depth of the lesion by a factor of 3.33 to 6 relative to using a cylindrical transducer.

Similarly, by using an applicator of the invention, as described above and implemented under the same electrical power supply conditions, it is possible by rotating the application head about its own axis and using emission for a duration of 7 min to 8 min, to give rise to a cylindrical lesion having an outside diameter of 10 mm to 12 mm.

In contrast, a prior art applicator having a cylindrical transducer of the kind described above, can obtain a cylindrical lesion with an outside diameter of 10 mm to 12 mm only with emission for a duration of 18 min to 20 min.

It can thus clearly be seen that implementing a plane transducer of the invention makes it possible advantageously, and other things being equal, to reduce the duration of the emission, and thus of the heating, by a factor of 1.5 to 2 compared with a cylindrical transducer.

The structural and functional characteristics provide a wide range of possibilities for using the applicator via an internal passageway, either endoscopically or using an intra-channel path, by constituting at least a portion of the element 2 in the form of a flexible sheath, or by percutaneous application using an element 2 in the form of a rigid tube.

To facilitate passing along the inside of a channel or the inside of an operative guide in an endoscope, the body 5 advantageously include a groove or passage 30 suitable for engaging a guide wire 31, thereby facilitating movement of the head 1 within a channel, particularly when the channel in question is of relatively small section and is subjected to changes of direction having small radius of curvature. Provision is also advantageously made to connect the rear portion 3 of the body 5 to a traction wire element 32 whose function is to make it possible, particularly when the sheath 2 is constituted by a helical winding of wire, to exert traction force on the applicator so as to enable it to be extracted from the inside of the channel or endoscope operative guide that it is occupying.

FIGS. 4 to 7 show a preferred industrial embodiment of the head 1 which comprises a body $5_1$ inserted in a tubular element $2_1$, of length beyond the rear portion $3_1$ that is appropriate for a typically endoscopic function or a typically endochannel function by being associated with a deformable flexible sheath that houses lines enabling the head 1 to be operated remotely, as in the preceding example.

Under such circumstances, although not shown, the tubular element $2_1$ has a window provided in register with the recess $6_1$, such a window being closed as in the preceding example by a membrane $21_1$.

In the embodiment of FIGS. 4 to 7, component elements that are the same as those in the preceding example, are given the same references in association with the subscript 1. In this embodiment, it is advantageously to provide notches or grooves 35 and 36 in the periphery of the body 5 to pass the wires 11 and 12, instead of using the hole 13.

In the above embodiments, it is assumed that the head 1 is fitted with a transducer 8 having one of its large faces in a position that is preferably parallel to the longitudinal axis of the body $5_1$.

It must be understood that the head can be fitted with a plurality of transducers 8 complying with a similar characteristic and mounted in similar manner so as to occupy all or part of the periphery of the body 5, each of them being situated in a position that is set back from said periphery so as to leave a cavity for coupling its emission face 17 via the cooling fluid. Under such circumstances, it should also be understood that each transducer is associated with means that enable ultrasound to propagate poorly or not at all and that are placed in register with the rear face 16 so as to enhance emission only of a useful near field via the face 17.

Thus, the head 1 can be fitted with two or three transducers, for example.

In accordance with the invention, it is also possible to envisage placing one or more transducers 8 so that they extend in a manner that is not parallel to the axis x—x', being inclined relative to said axis so that the near field that is emitted adopts a direction that is not normal to said axis.

It should also be understood that the probe can be provided with at least one transducer 8 extending perpendicularly to the axis x—x', being situated in the vicinity of its front portion 4. Under such circumstances, the membrane 21 can be implemented in the form of a balloon surrounding the transducer at a distance so as to define a protective volume in which a cooling liquid is confined that also performs ultrasound coupling.

Figure 7:
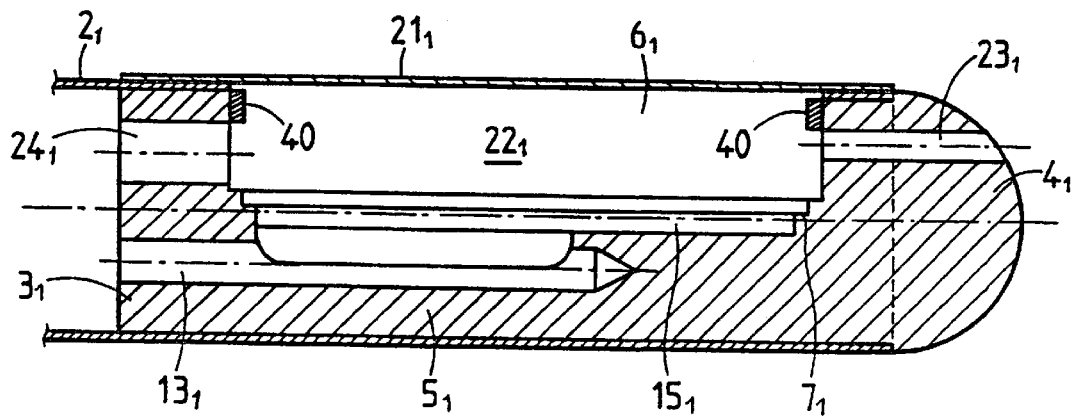
FIG. 7 is a section on discontinuous line VII—VII of FIG. 5.

FIG. 7 shows that it can be advantageous to cause the body 5 to include, e.g. in the recess 6, radio-opaque markers 40 making it possible to perform a fluoroscope marking function while moving the body into place endoscopically or within a channel.

In the above example, the applicator preferably comprises means for cooling the transducer. Nevertheless, the applicator could also be provided without any such cooling means.

Susceptibility Of Industrial Application

Use of the applicator is described above with reference to medical treatment. Nevertheless, the applicator can be used in any industrial application where it is necessary to provide local heating of a medium that absorbs ultrasound waves in a region that is situated at depth from the outside surface of the object to be treated.

For example, to destroy by means of heat a nest of parasites within a volume of wood or in a tree whose destruction is not desired, a heating method of the invention would consist in drilling a small diameter channel so as to allow the applicator to pass all the way to the nest. Naturally, such a channel would then constitute an artificial internal pathway for receiving the applicator.

Once the applicator of the invention has been put into position, the transducer is powered electrically at a given frequency for a predetermined length of time as a function of the nature of the nest of parasites and of the size thereof. Naturally, the transducer can be powered with electricity at multiple frequencies.

Depending on the volume of the nest of parasites, the transducer can be rotated so as to heat an annular region of greater extent. Such rotation can be continuous, alternating or otherwise, throughout the duration of the treatment, or it can be sequential and stepwise so as to heat contiguous zones of the region to be treated in succession.

The heating method of the invention can also be used for heating thermosetting resin injected in depth into a piece of wood in question, e.g. in the context of restoration.

The invention is not limited to the examples described and shown since various modifications can be made thereto without going beyond the ambit of the invention.

What is claimed is:

1. An ultrasound applicator for heating, via an internal path, an ultrasound absorbent medium, comprising:
   an application head having a longitudinal axis and including at least one ultrasonic transducer having a planar emission face and an opposite face, a leakproof membrane which overlays and is spaced from the emission face, and which is transparent to ultrasound, and means for preventing propagation of ultrasound from the opposite face;
   means for remotely connecting the transducer to an electricity generator; and
   means for providing ultrasound coupling with the membrane;
   the planar emission face being constructed and arranged to emit ultrasound waves through the membrane and in a direction that is substantially perpendicular to the emission face, such that the waves emitted are substantially planar and do not diverge in the vicinity of the transducer and the application head.

2. An applicator according to claim 1, further including means for rotating the transducer.

3. An applicator according to claim 2, wherein the means for rotating the transducer comprises the application head in a substantially cylindrical shape.

4. An applicator according to claim 1, further including means for cooling the transducer.

5. An applicator according to claim 4, wherein the head forms at least one cavity closed by the protective membrane, in which at least one ultrasonic transducer is disposed.

6. An applicator according to claim 5, wherein the head includes a duct connected to a line for feeding a cooling fluid that circulates over the emission face of the transducer and that occupies all of the volume defined by the cavity.

7. An applicator according to claim 6, wherein the head includes a second duct connected to a line for returning the cooling fluid.

8. An applicator according to claim 6, wherein the head is associated with means for measuring and regulating transducer temperature.

9. An applicator according to claim 6, wherein the head includes a hole for exhausting the cooling fluid to the outside of the applicator.

10. An applicator according to claim 1, further including a tubular element carrying the application head at one end and housing lines for connection to monitoring and/or power supply means.

11. An applicator according to claim 1, wherein the transducer has a planar emission face and a major dimension oriented parallel to the longitudinal axis of the head.

12. An applicator according to claim 11, wherein the transducer has a planar emission face parallel to the longitudinal axis of the head.

13. An applicator according to claim 11, wherein the transducer has a planar emission face at an angle with the longitudinal axis of the head.

14. An applicator according to claim 1, wherein the transducer has a planar emission face substantially normal to the longitudinal axis of the head.

15. An applicator according to claim 1, wherein the head is made of a material that is not ferromagnetic.

16. An applicator according to claim 1, wherein the protective membrane is in the form of an envelope that encloses at least in part an application cavity formed by the head and in which at least one ultrasound transducer is disposed.

17. An applicator according to claim 1, wherein the protective membrane is made in the form of a balloon enclosing an application cavity formed by the head and in which there is disposed at least one ultrasound transducer.

18. An applicator according to claim 1, wherein the means for preventing propagation comprises a leakproof chamber filled with air and formed by the head in co-operation with the opposite face of the transducer.

19. An applicator according to claim 1, wherein the head includes a through duct or passage substantially parallel to the longitudinal axis and constructed and arranged to engage a wire guide for travel within a channel.

20. An applicator according to claim 1, wherein the head is connected to a wire traction element.

21. An applicator according to claim 1, additionally comprising a tubular element formed from a flexible sheath, wherein the head is carried at the end of the tubular element.

22. An applicator according to claim 1, wherein the head carries at least one radio-opaque marker for performing a fluoroscopic marking function.

23. A method of heating a medium that absorbs ultrasound waves, comprising the steps of:
    placing in or close to said medium an applicator having at least one ultrasound transducer, the transducer having a planar emission face and emitting therefrom substantially planar ultrasound waves into the absorbent medium in a direction substantially perpendicular to the emission face, the waves not diverging in the vicinity of the transducer and the applicator; and
    emitting ultrasound waves from said transducer in order to heat the region of the absorbent medium that is situated in register with the emission face.

24. A method according to claim 23, further comprising causing the transducer to rotate.

25. A therapeutic method for treating a region of a human or animal body that absorbs ultrasound by means of hyperthermia, comprising the steps of:
    placing an applicator having at least one ultrasound transducer in or in the vicinity of the region to be treated, the transducer having a planar emission face for emitting into the ultrasound-absorbing region and in a direction substantially perpendicular to said emission face, ultrasound waves that are substantially planar, and that do not diverge in the vicinity of the transducer and the applicator; and emitting ultrasound waves from the transducer to heat the region situated in register with the emission face.

26. A method according to claim 25, further comprising causing the transducer to rotate.

* * * * *